United States Patent [19]
Matsushima et al.

[11] Patent Number: 5,925,352
[45] Date of Patent: Jul. 20, 1999

[54] METHOD OF TREATING INFLAMMATION WITH ANTIBODIES TO NEUTROPHIL CHEMOTACTIC FACTOR

[75] Inventors: Kouji Matsushima; Teizo Yoshimura, both of Frederick; Edward J. Leonard, Chevy Chase; Joost Oppenheim, Bethesda; Ettore Appella, Chevy Chase; Stephen D. Showalter, Frederick, all of Md.

[73] Assignee: The United States of America as represented by the Department of Health and Human Services, Washington, D.C.

[21] Appl. No.: 08/935,560

[22] Filed: Sep. 23, 1997

Related U.S. Application Data

[62] Division of application No. 08/467,612, Jun. 6, 1995, Pat. No. 5,698,196, which is a division of application No. 07/169,033, Mar. 16, 1988, Pat. No. 5,652,338.

[51] Int. Cl.$^6$ .................................................. A61K 39/395
[52] U.S. Cl. ..................... 424/158.1; 424/130.1; 424/145.1; 530/388.1; 530/388.23; 530/389.2; 514/885
[58] Field of Search ............................ 424/145.1, 158.1, 424/130.1; 530/388.23, 389.2, 388.1; 514/885

[56] References Cited

U.S. PATENT DOCUMENTS

| | | |
|---|---|---|
| 4,714,674 | 12/1987 | Palladino . |
| 4,797,277 | 1/1989 | Arfors . |
| 4,897,348 | 1/1990 | Johnson et al. . |
| 5,306,627 | 4/1994 | Yamada et al. . |
| 5,401,643 | 3/1995 | Yamada et al. . |
| 5,451,399 | 9/1995 | Gimbrone, Jr. et al. . |
| 5,652,338 | 7/1997 | Matsushima et al. . |
| 5,698,196 | 12/1997 | Matsushima et al. . |

FOREIGN PATENT DOCUMENTS

| | | |
|---|---|---|
| WO 89/04325 | 5/1989 | European Pat. Off. . |
| WO 89/04836 | 6/1989 | European Pat. Off. . |
| WO 89/10962 | 11/1989 | European Pat. Off. . |

OTHER PUBLICATIONS

Natanson et al. Annals of Internal Medicine, vol.:120 pp. 771–783, 1994.
Gregory et al., Biochemical and Biophysical Research Communications 151(2), pp. 883–890 (1988).
Walz et al., Biochemical and Biophysical Research Communications, vol. 149, No. 2, pp. 755–761 (1987).
Yoshimura et al., The Journal of Immunology, vol. 139, No. 3, pp. 788–793 (1987).
Tanaka et al., Fed. of European Biochem. Societies, vol. 236, No. 2, pp. 467–470 (1988).
Hickstein et al., Proc. Nat'l Acad. Sci. USA, vol. 86, pp. 257–261 (1989).
Schroder et al., The Journal of Immunology, vol. 139, No. 10, pp. 3474–3483 (1987).
Schmid et al., The Journal of Immunology, vol. 139, No. 1, pp. 250–256 (1987).
Yoshimura et al., Molecular Immunology, vol. 26, No. 1, pp. 87–93 (1989).
Yoshimura et al., Proc. Nat'l Acad. Sci. USA, vol. 84, pp. 9233–9237 (1987).
Von Damme et al., J. Exp. Med., vol. 167, pp. 1364–1376 (1988).
Matsushima et al, J. Exp. Med., vol. 167, pp. 1883–1893 (1988).
Shimizu et al., Scand. J. Immunol. vol. 28, pp. 675–685 (1988).
Kownatzki, et al., Clin. Exp. Immunol., vol. 64(1), pp. 214–227 (1986).

*Primary Examiner*—Prema Mertz
*Attorney, Agent, or Firm*—Morgan & Finnegan, L.L.P.

[57] ABSTRACT

An isloated, synthetic preparation of a novel neutrophil-specific chemotactic factor (NCF), monoclonal antibodies having specific binding affinity for NCF and a clone containing the complete cDNA coding sequence for NCF are disclosed.

2 Claims, 5 Drawing Sheets

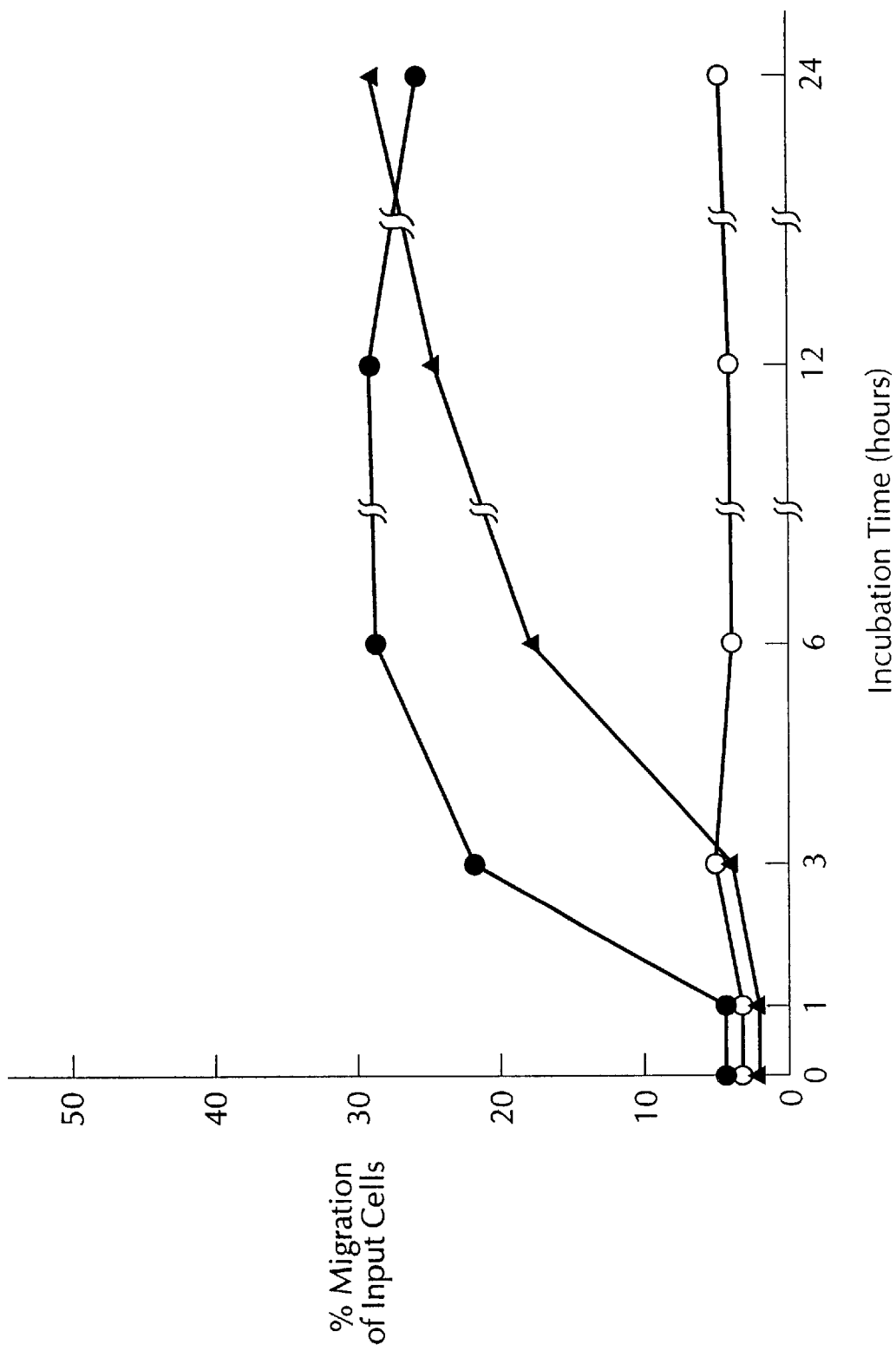

5,925,352

METHOD OF TREATING INFLAMMATION WITH ANTIBODIES TO NEUTROPHIL CHEMOTACTIC FACTOR

This is a divisonal of application Ser. No. 08/467,612 filed Jun. 6, 1995, now U.S. Pat. No. 5,698,196, which is a divisional of application Ser. No. 07/169,033, filed Mar. 16, 1988, now U.S. Pat. No. 5,652,338.

BACKGROUND OF THE INVENTION

1. Technical Field

The present invention relates to an isolated, synthetic preparation of a novel neutrophil-specific chemotactic factor (NCF), monoclonal antibodies having specific binding affinity for NCF and a clone containing the complete coding sequence for NCF.

2. State of the Art

Activated monocytes/macrophages produce various mediators that cause inflammation. Among them are chemotactic factors which cause white blood cells to migrate into inflammatory sites where these factors area released. Neutrophils, the dominant leukocytes attracted by the chemotactic factors, are believed to play a critical role in the inflammatory reactions. Such diseases as rheumatoid arthritis, idiopathic pulmonary fibrosis and certain pathological inflammatory changes in many other conditions are believed to be caused by neutrophils and/or their products. However, a specific pro-inflammatory mediator released by tissue macrophages and other cells in response to imflammatory stmuli and leading to neutrophil-rich leukocyte accumulation in host defense and disease, has not heretofore been identified and isolated.

SUMMARY OF THE INVENTION

It is, therefore, an object of the present invention to provide a biologically active novel synthetic polypeptide acting as a neutrophil-specific chemotactic factor (NCF).

It is a further object of the present invention to provide a molecular clone containing the complete coding sequence for the synthesis of NCF by either prokaryotic or eukaryotic expression vectors.

It is a still further object of ,the present invention to provide monoclonal antibodies having specific binding affinity for NCF of the present invention.

It is another object of the present invention to provide a kit comprising a container containing the cDNA for NCF quantitation, detection or localization of NCF mRNA in a body sample.

It is yet another object of the present invention to provide a kit comprising a container containing anti-NCF antibodies having specific binding affinity for NCF for quantitation, detection or localization of NCF in a body sample.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIGS. 2A–2D shows:

Figure 1:
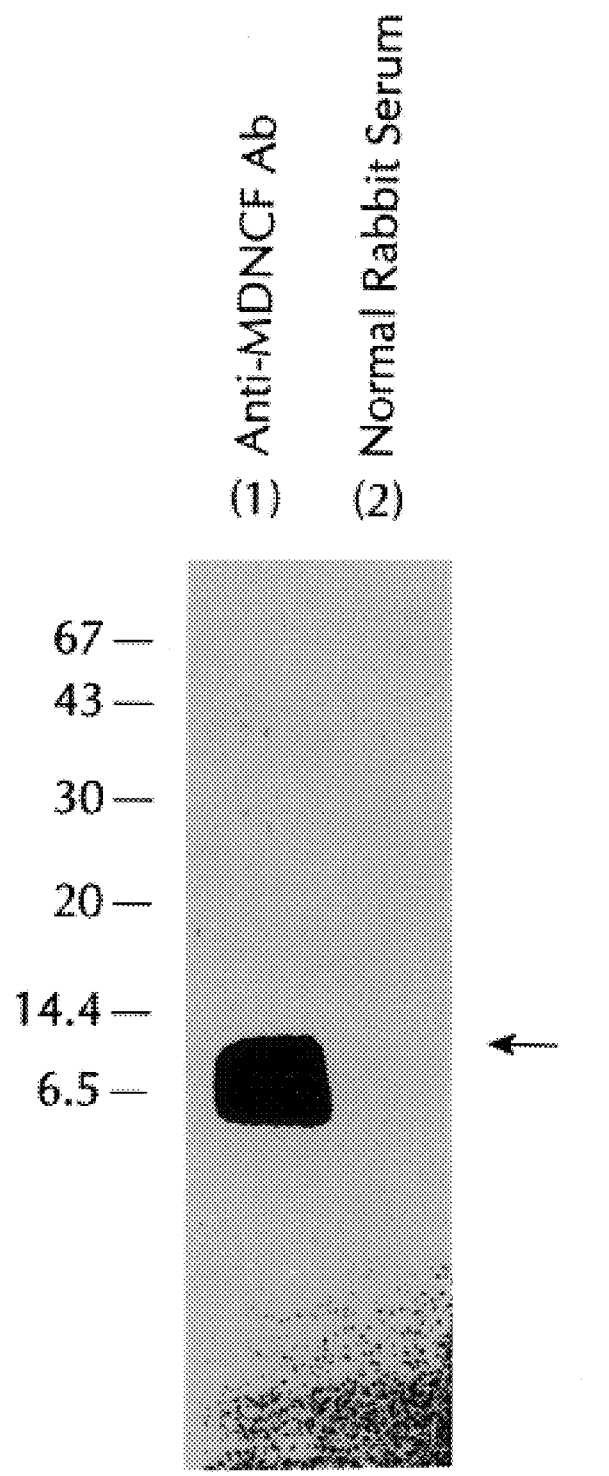
FIG. 1 demonstrates translation of cDNA into NCF protein in reticulocyte lysate system.

(a) Northern blot analysis of mRNA induction in lipopolysaccharide (LPS) stimulated peripheral blood monomuclear cells (PBMC);

(b) The time course of the accumulation of neutrophil chemotactic activity in culture media of PBMC after stimulation with LPS;

(c) Induction of NCF mRNA in PBMC by IL 1 or TNF, but not by IL 2, gamma-IFN, and alpha-IFN;

(d) HPLC gel filtration analysis of IL 1 and TNF induced neutrophil chemotactic activity.

DETAILED DESCRIPTION OF THE INVENTION

The above and various other objects and advantages of the present invention are achieved by a homogeneously pure, isolated, synthetic neutrophil chemotactic protein, designated herein NCF, composed in the whole or in part only of the following amino acid sequence (single letter code):

$NH_2$-S-A-K-E-L-R-C-Q-C-I-K-T-Y-S-K-P-F-H-P-K-F-I-K-E-L-R-V -I-E-S-G-P-H-C-A-N-T-E-I-I-V-K-L-S-D-G-R-E-L-C-L-D-P-K-E-N-W-V-Q-R-V-V-E-K-F-L-K-R-A-E-N-S

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

Chemical synthesis of the NCF of the present invention composed of the 72 amino acid residues as shown above, is achieved by commercially available polypeptide synthesizers. Alternatively, the NCF of the present invention is synthesized by standard techniques employing an expression vector containing in its genome the cloned complete coding sequence of NCF. Anti-NCF monoclonal antibodies of the present invention are prepared by standard hybridoma technology and utilized for purification and assaying purposes following standard immunological methodologies well known in the art.

High performance liquid chromatography (HPLC), in situ hybridization assays, Northern blotting analyses and the like are typical examples of the standard conventional techniques well known to one of ordinary skill in the art, which can be employed for isolation, localization, differentiation, detection, or measurement of the mRNA for NCF in biological samples.

It should be noted that the fact that chemically synthesized polypeptide of the present invention at 10 nanomolar concentrations acts as a neutrophil attracting factor, is shown by the results presented in Table 1.

TABLE 1

Chemotactic response of human neutrophils to chemically synthesized NCF.

| Concentration of NCF, nanomolar | Percentage of assay neutrophils that migrated |
|---|---|
| 1000 | 23 |
| 100 | 34 |
| 10 | 32 |
| 1 | 5 |
| 0.1 | 1 |
| Hanks medium | 0.3 |
| $10^{-7}$M fMet-Leu-Phe | 40 |

1. It is typical for chemoattractant dose-response curves to show an optimum, with a decreased response at concentrations above the optimum.
2. fMet-Leu-Phe is a commonly used reference chemoattractant.

It may be pointed out that various stimuli cause the release or secretion of more than one chemoattractant. Without the cDNA of the present invention, it is clear, of course, that the presence, specificially of the mRNA for NCF as an involved factor in a particular clinico-pathological situation, could not be definitively identified and diagnosed. cDNA of the present invention due to its binding affinity for mRNA for NCF, for the first time makes it possible to analyze body samples such as joint fluid, sputum, alveolar lavage fluid, tissue samples and the like to detect the presence or absence of mRNA for NCF. Of course, the antibodies can also be utilized for diagnostic purposes to detect the NCF and to neutralize the NCF for alleviating any disease or anomalous conditions in which the presence of NCF is found to be a causative factor.

A pharmaceutical composition for use in treating inflammatory condition comprises and anti-inflammatory effective amount of the anti-NCF monoclonal antibodies in pharmaceutically acceptable carrier, such as physiological saline, sterile non-toxic buffer and the like.

A deposit of cDNA for NCF and of the hybridoma for anti-NCF monoclonal antibodies have been made at the ATCC, 10801 University Boulevard, Manassas, Va. 20110-2209 on Jan. 12, 1988 and Feb. 17, 1988, respectively, under the accession numbers 40412 and HB9647, respectively. The deposits shall be viably maintained, replacing if they became non-viable, for a period of 30 years from the date of the deposit, or for 5 years from the last date of request for a sample of the deposit, which is longer, and made available to the public without restriction in accordance with the provisions of the law. The Commissioner of Patents and Trademarks, upon request, shall have access to the deposits.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of treating an inflamrnatory condition, said method comprising administering to a host inflicted with an inflammnatory condition caused by or related to neutrophil chemotactic factor (NCF) polypeptide, an antiinflammatory effective amount of anti-NCF antibodies, wherein said antibodies have specific binding affinity for a neutrophil chemotactic factor polypeptide or part thereof where the polypeptide comprises the following amino acid sequence represented by single letter code;

$NH_2$-S-A-K-E-L-R-C-Q-C-I-K-T-Y-S-K-P-F-H-P-K-F-I-K-E-L-R- V-I-E-S-G-P-H-C-A-N-T-E-I-I-V-K-L-S-D-G-R-E-L-C-L-D-P-K-E-N-W-V-Q-R-V-V-E-K-F-L-K-R-A-E-N-S.

2. The method of claim 1, wherein said antibodies are monoclonal antibodies.

\* \* \* \* \*

UNITED STATES PATENT AND TRADEMARK OFFICE
CERTIFICATE OF CORRECTION

PATENT NO. : 5,925,352
DATED : July 20, 1999
INVENTOR(S) : Matsushima, et al.

It is certified that error appears in the above-identified patent and that said Letters Patent is hereby corrected as shown below:

On the title page, item [57];

In line 1 of the Abstract, "isloated" should read "isolated"

Column 2, line 4, "shows" should read "show"

Figure 2A:
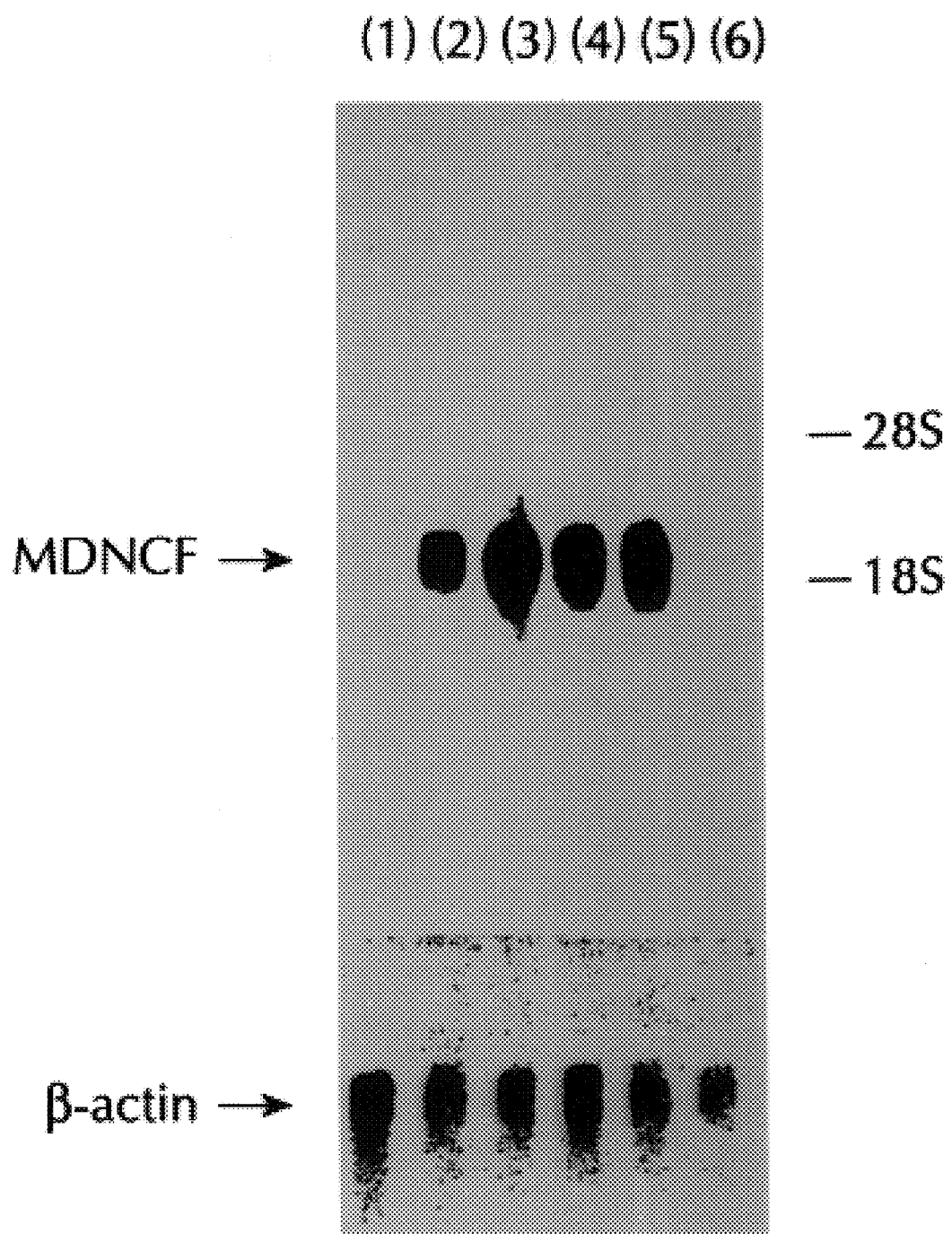

Column 2, line 6 "(a)" should read "(Fig. 2A)"

Column 2, line 9 "(b)"should read "(Fig. 2B)"

Column 2, line 12 "LPS;" should read "LPS; cells ($5 \times 10^6$) were cultured in 1 ml medium with or without 10 ug/ml LPS for 1, 3, 6, 12 and 24 hours. LPS-supernatant (●—●); LPS-supernatant 1/3 dilution (▲—▲); control supernatant (O—O)"

Figure 2C:
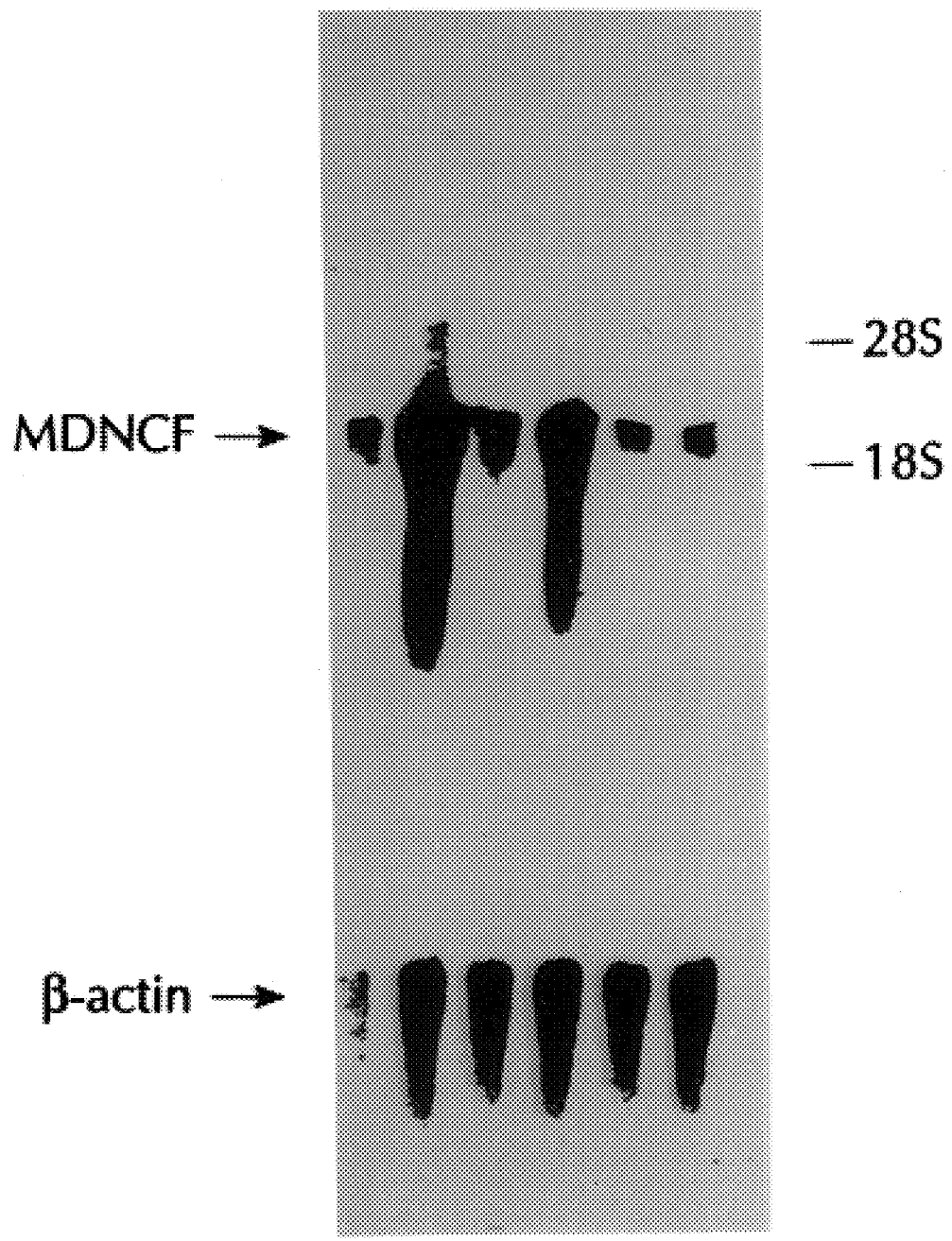

Column 2, line 13, "(c)" should read "(Fig. 2C)"

Figure 2D:
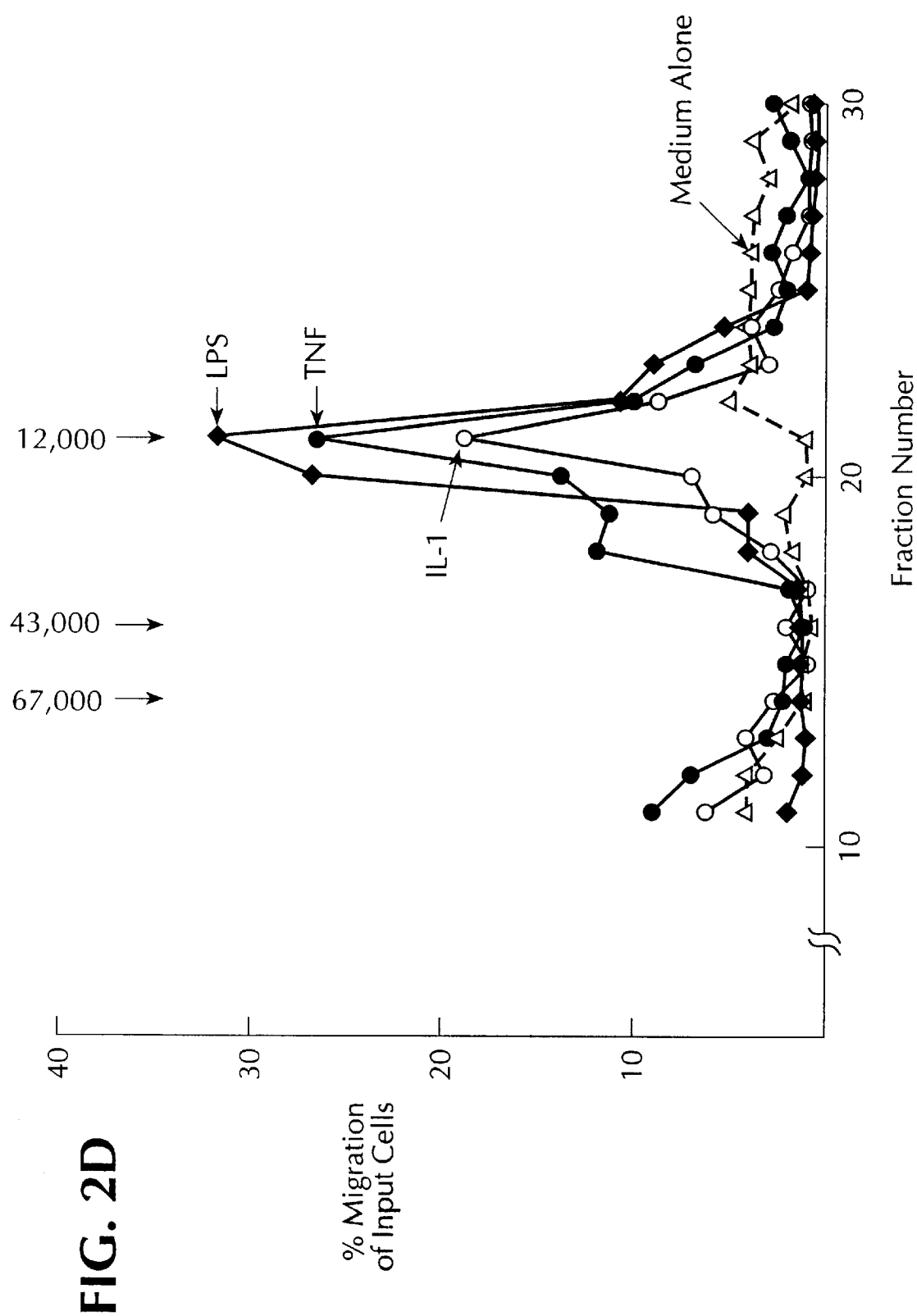

Column 2, line 15, "(d)" should read "(Fig. 2D)"

UNITED STATES PATENT AND TRADEMARK OFFICE
CERTIFICATE OF CORRECTION

Page 2 of 2

PATENT NO. : 5,925,352
DATED : July 20, 1999
INVENTOR(S) : Matsushima, et al.

It is certified that error appears in the above-identified patent and that said Letters Patent is hereby corrected as shown below:

Column 4, line 20, "inflamrnatory" should read "inflammatory"

Column 4, line 22, "inflammnatory" should read "inflammatory".

Signed and Sealed this

Thirteenth Day of June, 2000

*Attest:*

Q. TODD DICKINSON

*Attesting Officer*  *Director of Patents and Trademarks*